United States Patent
Kane et al.

(10) Patent No.: US 7,371,689 B2
(45) Date of Patent: May 13, 2008

(54) BACKSIDE UNLAYERING OF MOSFET DEVICES FOR ELECTRICAL AND PHYSICAL CHARACTERIZATION

(75) Inventors: Terence L Kane, Wappingers Falls, NY (US); Darrell L Miles, Wappingers Falls, NY (US); John D Sylvestri, Poughkeepsie, NY (US); Michael P Tenney, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 223 days.

(21) Appl. No.: 11/242,719

(22) Filed: Oct. 3, 2005

(65) Prior Publication Data

US 2006/0030160 A1  Feb. 9, 2006

Related U.S. Application Data

(63) Continuation of application No. 10/752,162, filed on Jan. 6, 2004, now Pat. No. 7,015,146.

(51) Int. Cl.
*H01L 21/302* (2006.01)

(52) U.S. Cl. .............................. 438/710; 257/E21.218; 257/492.3; 156/345.39

(58) Field of Classification Search ................ 438/710, 438/712, 715; 250/492.2, 492.3; 156/345.39; 257/E21.218
See application file for complete search history.

(56) References Cited

U.S. PATENT DOCUMENTS 4,411,762 A  10/1983  Kline .......................... 205/96

4,503,329 A  3/1985  Yamaguchi et al. ........ 250/309
5,319,197 A  6/1994  Friedhelm .................... 250/305

(Continued)

FOREIGN PATENT DOCUMENTS

JP       H04-059049       2/1992

(Continued)

OTHER PUBLICATIONS

R. Desplats, F. Beaudoin, P. Perdu, *CNC Milling and Polishing Techniques for Backside Sample Preparation*, CNES-THALES Laboratory-18 avenue Edouard BELIN-31401 Toulouse Cedex 4-France, pp. 1-9.

(Continued)

*Primary Examiner*—Hsien-ming Lee
(74) *Attorney, Agent, or Firm*—DeLio & Peterson, LLC; Kelly M. Nowak; Steven Capella

(57) ABSTRACT

A method and system for backside unlayering a semiconductor device to expose FEOL semiconductor features of the device for subsequent electrical and/or physical probing. A window is formed within a backside substrate layer of the semiconductor. A collimated ion plasma is generated and directed so as to contact the semiconductor only within the backside window via an opening in a focusing shield. This focused collimated ion plasma contacts the semiconductor, only within the window, while the semiconductor is simultaneously being rotated and tilted by a temperature controlled stage, for uniform removal of semiconductor layering such that the semiconductor features, in a location on the semiconductor corresponding to the backside window, are exposed. Backside unlayering of the invention may be enhanced by CAIBE processing.

14 Claims, 6 Drawing Sheets

U.S. PATENT DOCUMENTS

| | | | | |
|---|---|---|---|---|
| 5,653,622 | A | 8/1997 | Drill et al. | 451/5 |
| 5,698,474 | A | 12/1997 | Hurley | 438/15 |
| 5,916,424 | A | 6/1999 | Libby et al. | 204/298.36 |
| 5,926,688 | A | 7/1999 | Lee et al. | 438/4 |
| 6,211,527 | B1 | 4/2001 | Chandler | 290/492.2 |
| 6,263,566 | B1 | 7/2001 | Hembree et al. | 29/974 |
| 6,346,768 | B1 | 2/2002 | Proudfoot | 313/359.1 |
| 6,570,170 | B2 | 5/2003 | Moore | 250/492.4 |
| 6,590,409 | B1 | 7/2003 | Hsiung et al. | 524/765 |
| 2002/0072308 | A1 | 6/2002 | Kane et al. | 451/41 |
| 2003/0073314 | A1* | 4/2003 | Skinner et al. | 438/689 |

FOREIGN PATENT DOCUMENTS

| | | |
|---|---|---|
| JP | H06-209142 | 6/1994 |
| JP | 2001-518694 | 10/2001 |
| JP | 2002-500808 | 1/2002 |
| JP | 2004-536288 | 12/2004 |
| JP | 2001-168070 | 1/2008 |

OTHER PUBLICATIONS

R. Livengood, P. Winer, J.A. Giacobbe, J. Stinson, J.D. Finnegan, *Advanced Micro-Surgery Techniques and Material Parasitics for Debug of Flip-Chip Microprocessor*, Proceeding from the 25th International Symposium for Testing and Failure Analysis, Nov. 14-18, 1999, Santa Clara, CA, Intel Corporation, Santa Clara, CA, pp. 477-483.

J.P. Huynh, J.P. Shannon, R.W. Johnson, M. Santana, Jr., T.Y. Chu, M. Gonzalez, *Backside FIB Device Modifications Through the BOX Layer of an SOI Device*, Proceedings from the 28th International Symposium for Testing and Failure Analysis, Nov. 3-7, 2002, Phoenix, AZ, Advanced Micro Devices, Inc., Austin, TX, pp. 403-407.

V. Korchnoi, Dr. A. Fenigstein, A. Barger, *Silicon Trenching Using Dry Etch Process for Back Side FIB and Probing*, Proceeding from the 26th International Symposium for Testing and Failure Analysis, Nov. 12-16, 2000, Bellevue, WA, Intel Corporation, Israel pp. 559-565.

P.F. Ullmann, C.C. Talbot, R.A. Lee, C. Orjuela, R. Nicholson, *A New Robust Backside Flip-Chip Probing Methodology*, Proceedings of the 22nd International Symposium for Testing and Failure Analysis, Nov. 18-22, 1996, Los Angeles, CA, Schlumberger Technologies, San Jose, CA, pp. 381-386.

S. Silverman, R. Aucoin, J. Mallatt, D. Ehrlich, *Laser Microchemical Technology; New Tools for Flip-Chip Debug and Failure Analysis*, Proceedings from the 23rd International Symposium for Testing and Analysis, Oct. 27-31, 1997, Santa Clara, CA, Revise Inc., Burlington, MA, pp. 211-213.

C-L. Chiang, N. Khurana, D.T. Hurley, K. Teasdale, *Backside Emission Microscopy for Integrated Circuits on Heavily Doped Substrate*, Proceedings from the 24th International Symposium for Testing and Failure Analysis, Nov. 15-19, 1998, Dallas, TX, Hypervision, Inc., Fremont, CA, Hexfet America, Temecula, CA, 1998 ASM International.

P. Perdu, R. Desplats, F. Beaudoin, *Comparative Study of Sample Preparation Techniques for Backside Analysis*, Proceedings from the 24th International Symposium for Testing and Failure Analysis, Nov. 12-16, 2000, Bellevue, WA, Toulouse, France, pp. 161-171.

* cited by examiner

BACKSIDE UNLAYERING OF MOSFET DEVICES FOR ELECTRICAL AND PHYSICAL CHARACTERIZATION

This is a continuation of application Ser. No. 10/752,162, filed on Jan. 6, 2004, which issued as U.S. Pat. No. 7,015,146 on Mar. 21, 2006.

BACKGROUND OF THE INVENTION

1. Field of the Invention

The present invention relates to an apparatus and processes for backside thinning of MOSFET devices as a fully packaged die or in a wafer-to-wafer fragment form.

2. Description of Related Art

Advanced semiconductor technology including Ultra Large Scale Integrated circuits (ULSI), Bipolar-CMOS hybrid devices (BICMOS), Microelectronic Mechanical Systems (MEMS), and the like, employ a diversity of semiconductor materials such as, for example, silicon, silicon on insulator, strained silicon junction, silicon germanium, germanium, gallium arsenide, and the like. These advanced semiconductor technologies involve increasingly shrinking feature sizes, thinner gate dielectric film thickness and high-k dielectric constant gate layers combined with the complexity of strained silicon shallow junctions, buried oxide SOI films (with thinner buried oxide films to reduce capacitance), bonded wafer substrates, and the like.

The difficulties of accessing front end of line (FEOL) device structures for device measurements, device chip repair, device design verification, and device electrical and physical characterization, while maintaining both device functionality and integrity, through back-end-of the-line (BEOL) unlayering dictates accessing the device being investigated through a backside, i.e., chip die substrate unlayering. Flip chip die attachment to module substrate further necessitates this backside approach in order to maintain full functionality of the module under investigation.

Conventional techniques for backside access to FEOL devices include global thinning of the silicon substrate, followed by wet etch removal of the buried oxide layer for access to the desired FEOL device, or by reactive ion etch or plasma etch. The wet etch approach may involve, for example, BEOL unlayering via the application of a mixture of de-ionized water and hydrofluoric acid, following by application of cesium hydroxide heated to an elevated temperature to remove substrate layers from the backside of the device for exposing a buried oxide layer for access to FEOL devices. In an alternate conventional backside unlayering approach, focused ion beam microscopy (FIB) is used to unlayer the device from the backside to open a window in the silicon substrate and the buried oxide layer for access to the FEOL device. Alternatively, laser micro chemical (LMC) processing may be applied for removal of silicon or polysilicon materials.

However, these conventional approaches of wet etch, FIB microscopy for backside unlayering or LMC to access FEOL devices are plagued by a number of drawbacks.

In the instance of laser microchemical (LMC) removal, only silicon and polysilicon materials can be selectively removed. For wet etch processing, the uncontrollability of certain wet etch chemistries in BEOL unlayering often results in attack of both the buried oxide layer and underlying layers not intended for removal. Wet chemistries also involve ionic species that are often residually left on the device. The residues of these wet chemistries can cause leakage paths and/or shorts in the device being unlayered. In addition, wet etch chemistries often undercut surrounding layers of the area of the device under investigation, such that these undercuts adversely affect junction regions, alter the strain silicon junctions, as well as change the electrical and physical properties of the device being unlayered. Further, the uncontrolled nature of wet etchants may result in non-uniform removal of the buried oxide layer, leaving behind regions where the buried oxide layer is not completely removed and other areas where device regions are exposed or overetched.

Backside unlayering for access to FEOL devices using conventional FIB microscopy approaches also has several limitations and shortcomings. For instance, the high acceleration beam voltages, such as those of 6 keV to 50 keV, can charge localized regions of the device under investigation such that damage occurs to the thin gate oxides or high-k films. Also, the high atomic number of gallium ions used in FIB associated with the liquid gallium source may interact with the device being processed such that leakage paths and/or shorts occur in the device or alter the threshold voltage device characteristics. The etch chemistries of the gases used in FIB processing, such as, $XeF_2$, $Br_2$, $Cl_2$, can also lead to undesirable leakage paths, shorts, and shifts in threshold voltage characteristics of the device undergoing FIB processing.

Thus, as the thickness of buried oxide films continue to decrease with advanced technologies, such as those devices having buried oxide film thickness ranging from between 1100 Angstroms to 550 Angstroms (or lower), the proximity of the highly energetic accelerating FIB beam to the FEOL device imposes limitations on the ability of opening windows from the backside of the buried oxide for access to the FEOL device. In addition, the heat generated by the high atomic number in ion beam at the site where the FIB beam is incident on the region of the device being processed can easily alter, change, or modify the electrical characteristics, as well as affect the strain silicon junction regions of the FEOL device being processed.

In addition to the above problems associated with conventional backside unlayering, other problems associated with conventional topdown unlayering techniques for access to the FEOL device become even more prominent when high numbers of BEOL interconnection levels, e.g., eight or more copper interconnection layers, are present on the device undergoing topdown processing. Also complicating any attempt for circuit side unlayering for access to FEOL structures is the combination of BEOL low-k (i.e. k<2.5) interlevel dielectric films, such as those with low modulus physical properties, as well as the presence of hard mask film layers employed as etch stop layers during chemical mechanical planarization (CMP) processing.

For example, results of a SOI MOSFET after conventional backside unlayering processing via chemical etch removal and heat are shown in FIGS. 1 and 2. The chemical etch unlayering to remove the buried oxide layer of the SOI region results in isotropic chemical etch attack causing undercutting, damage and non planar etch removal, collectively shown as 200, of the MOSFET active implant regions 123. The isotropic chemical etch attack also extends beyond the active silicon implant junction regions to damage 201 the buried oxide layer 126. FIG. 2 illustrates, from a backside view, entire regions of undercut and damaged implant areas of the MOSFET of FIG. 1 as a result of such conventional chemical etch removal unlayering. In addition, conventional backside unlayering processing also commonly attack the liner region between the shallow trench insulator and the active silicon implanted regions. Conventional chemical isotropic etch methods result in selective etching of the circumferential region around interconnection vias extending down to the active silicon implant region. This in turn, results in undercutting and damage 200, 201 of implant areas rendering the SOI MOSFET of FIGS. 1 and 2 non-functional for any subsequent electrical characterization by sub-micron atomic force microscopy contact measurements, non contact capacitive measurements or by sub micron tungsten wire contact probing.

In addition, alternative methods utilizing laser assisted chemical etching for backside thinning are limited to unlayering of silicon films or polysilicon films, and are generally not efficient for unlayering of silicon oxide, buried oxide layers, shallow trench insulator films (typically oxide or tetraorthosilicate films), as well as substrate materials including germanium, gallium arsenide, and silicon germanium materials.

Still other known techniques for access to FEOL devices include those that involve non-contact methods of semiconductor backside analysis such as, but not limited to, emission microscopy, infrared wavelength imaging, light induced voltage alteration (LIVA), thermal induced voltage alteration (TIVA), optical beam induced resistance change (OBIRCH), and optical induced beam current (OBIC). These no contact methods of analysis are dependent on backside thinning of heavily doped substrate materials to permit backside imaging. However, such backside imaging does not require full backside unlayering to the active silicon (i.e., shallow junction implant regions) or the exposure of the tungsten interconnect vias, and as such, electrical characterization thereof cannot be accomplished.

Accordingly, as device geometries continue to shrink in size, further improvements are required for backside unlayering to access smaller FEOL devices for the electrical characterization thereof, while maintaining device integrity, reliability and functionality.

SUMMARY OF THE INVENTION

Bearing in mind the problems and deficiencies of the prior art, it is therefore an object of the present invention to provide a method and apparatus for die or wafer backside unlayering, prior to electrical probing and/or characterization of a site specific MOSFET device, that avoids damaging or rupturing the gate film, particularly gate films less than about 2 nm in thickness, and/or high dielectric constant gate films (i.e., greater than about 10).

Another object of the present invention is to provide a method and apparatus die/wafer backside unlayering of films including, but not limited to, silicon oxide, buried oxide layers, shallow trench insulator films (e.g., oxide or tetraorthosilicate films), germanium, gallium arsenide, and silicon germanium materials, as well as substrate layers including bulk silicon, bonded SOI substrate materials, strained silicon, and shallow junctions (e.g. those less than about 80 nm), Yet another object and advantage of the invention is to provide apparatus and methods that eliminate any affects induced by surface amorphization damage associated with high accelerating beam potential (>1 KeV to 300 KeV) of conventional FIB microscopy processing.

Still another object of the present invention is to provide a planar unlayering process that compensates for non-uniform, irregular FEOL features and/or layers as viewed or unlayered from the backside of the die or wafer.

A further object and advantage of the invention is to provide apparatus and methods that avoid any charge-induced damage associated with RF plasma sources or those associated with focus ion beam systems.

Other objects and advantages of the invention will in part be obvious and will in part be apparent from the specification.

The above and other objects and advantages, which will be apparent to one skilled in the art, are achieved in the present invention, which is directed to, in a first aspect, a method of processing a backside of a semiconductor device by providing a semiconductor having a backside surface within a processing chamber. A window is formed in the backside surface of the semiconductor, and then a collimated ion plasma is generated within such processing chamber. This collimated ion plasma is focused so as to contact the semiconductor only within the window by passing the collimated ion plasma through an opening in a shield within the processing chamber. The focused collimated ion plasma then contacts the semiconductor only within the window for the uniform removal of semiconductor layering such that the semiconductor features, in a location on the semiconductor corresponding to the backside window, are exposed.

In another aspect, the invention is at least directed to a method of processing a backside of a semiconductor device by providing a processing chamber having a rotating, tilting stage. A semiconductor, having at a back side thereof a substrate layer over an insulator layer, is provided within the chamber. The insulator layer of this semiconductor includes a plurality of semiconductor features therein. The semiconductor is positioned in the chamber on the rotating, tilting stage, and then a window is formed extending into the substrate layer at the semiconductor backside. A collimated ion plasma is generated in the chamber, and then passes through an opening in a shield within the processing chamber for focusing the collimated ion plasma such that it only contacts the semiconductor within the backside window. The focused collimated ion plasma contacts the semiconductor in the window while simultaneously rotating and tilting the semiconductor on the stage. This enables uniform removal of any remaining substrate layer as well as the insulator layer within the window for exposing selected ones of the plurality of semiconductor features for a subsequent processing step.

In still another aspect, the invention is at least directed to a system for processing a backside of a semiconductor device. The system includes a processing chamber with a semiconductor therein. This semiconductor has a plurality of layers and a window located at its backside. An ion source is within the processing chamber, as well as at least first and second collimators. Within the processing chamber, the collimators are located between the ion source and the semiconductor. A shield having an opening is the chamber, between the collimators and the semiconductor, such that the system generates a collimated ion plasma which is focused through the opening so as to only contact the semiconductor within the backside window. This advantageously enables uniformly removing selected ones of the plurality of semiconductor layers exposed through the window, such that FEOL semiconductor features of the semiconductor are exposed for probing.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
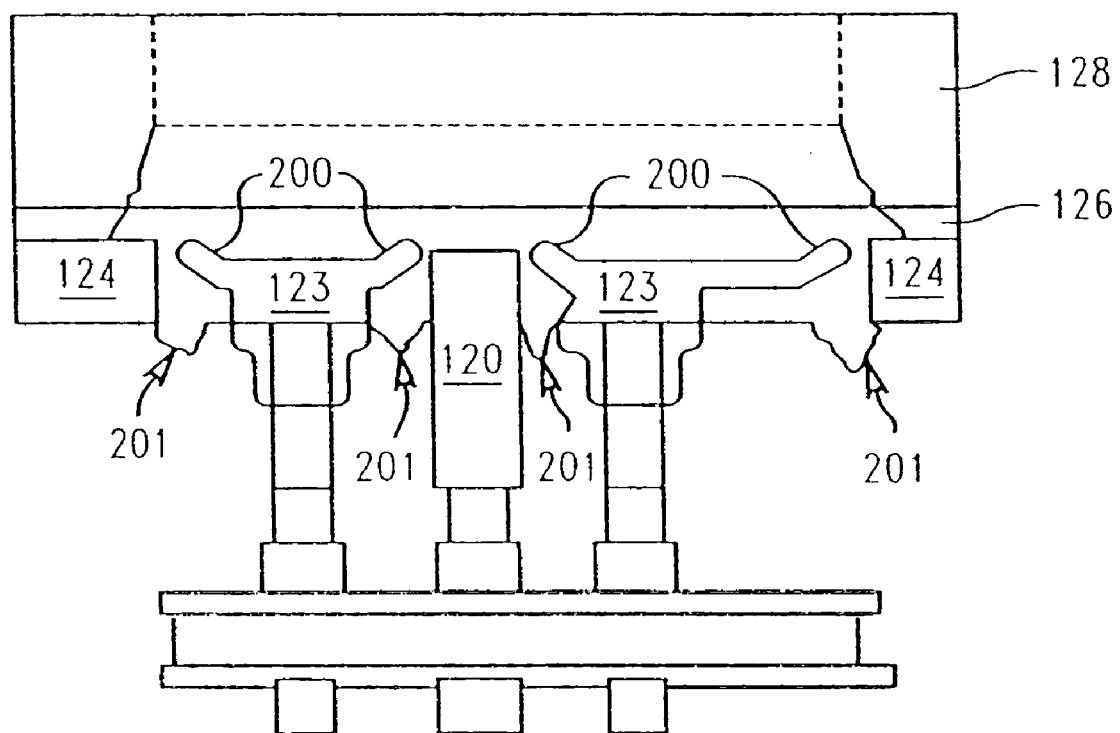
FIG. 1 is a prior art cross section illustration of a SOI MOSFET processed by conventional chemical etch unlayering methods to remove the buried oxide layer of the SOI region whereby the chemical etchant extends past the active silicon implant junction regions and selectively etches the region around the interconnection via resulting in a structurally and electrically damaged MOSFET device.

In describing the preferred embodiment of the present invention, reference will be made herein to FIGS. 3A-6 of the drawings in which like numerals refer to like features of the invention. Features of the invention are not necessarily shown to scale in the drawings.

The present invention is directed to an apparatus and processes for backside thinning of semiconductor devices, either as a fully packaged die or in wafer to wafer fragment form. In the invention, the backside of the structure for processing in accordance with the invention may be a backside of a semiconductor device, wafer, wafer fragment, die, packaged die and the like.

Preferably, the apparatus and methods of the invention are utilized for backside thinning, or unlayering, of a site specific MOSFET device in a packaged die, or from a wafer fragment while maintaining MOSFET device electrical functionality. These MOSFET devices may include, but not limited to, sub-130 nanometer node CMOS BICMOS, SiGe, Gallium Arsenide, technologies. Substrate materials involved in these technologies may include bulk silicon, silicon on insulator (SOI), strained silicon (SE), polysilicon, silicon oxide, silicon germanium, germanium, gallium arsenide, buried oxide layers, shallow trench insulator films, and the like.

Still further, the present invention may be used to backside unlayer FEOL structure films that are non-planar, comprised of dissimilar materials, or even both, to enable selective backside delayering of a site specific MOSFET device for subsequent electrical characterization thereof. These dissimilar, non planar films may include, but are not limited to, tungsten, titanium nitride, silicon nitride, heavily doped silicon, buried oxide films, shallow trench insulator films, high density plasma deposited oxide, high density plasma deposited nitride, chemical vapor deposited tetraorthosilicate films, and the like.

A critical feature of the present backside unlayering of a site specific MOSFET device is that it maintains the electrical integrity of this site specific MOSFET device to enable subsequent electrical characterization and physical analysis. For example, the invention advantageously permits subsequent sub micron contact probing, such as for example, via contacting Atomic Force Microscopy (AFM), Scanning Probe Microscope (SPM), Atomic Force Probing (AFP), and non-contact probing (AFM and SPM) of the exposed FEOL structures composing MOSFET devices. Measurement of electrical anomalies in MOSFET devices employing the apparatus and methods of the present backside unlayering approach advantageously permits further refinement in process simulation models and optimization of MOSFET device designs, as well as improvements in reliability and process yields.

For ease of understanding the invention, reference is made to FIGS. 3A-6, however, it should be appreciated that the foregoing invention may be applied to a variety of differing semiconductor technologies as discussed above.

Figure 3A:
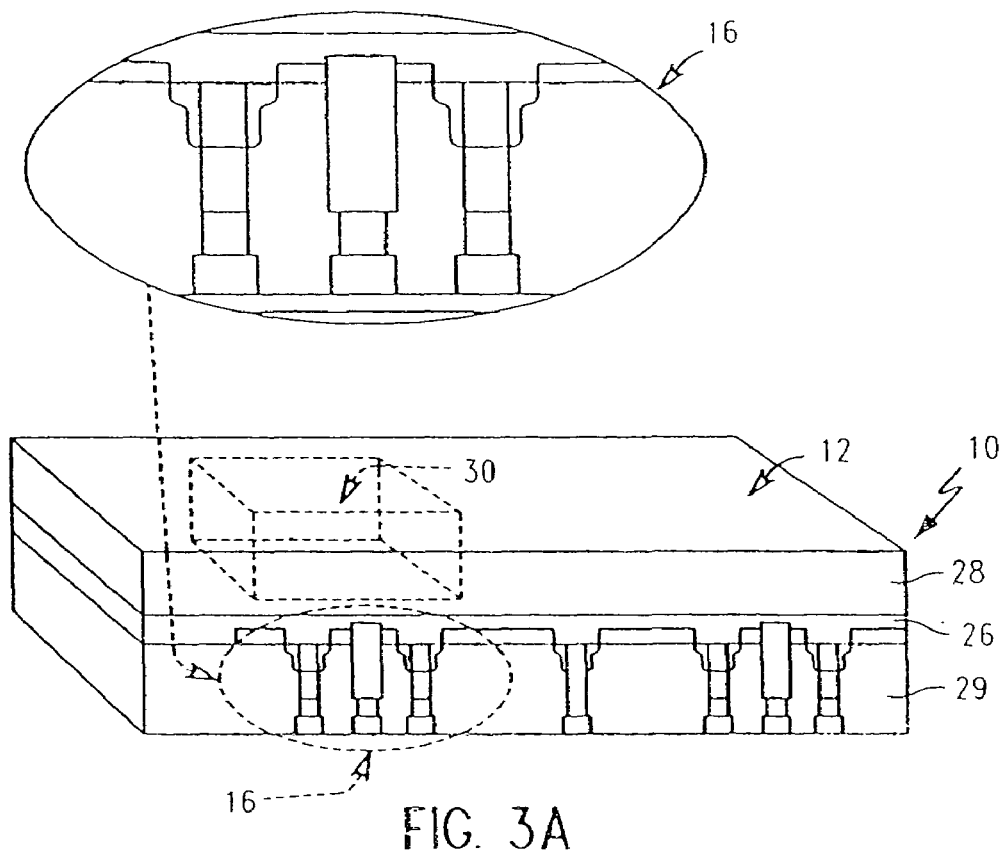
FIG. 3A is an oblique view of a backside unlayered region of a semiconductor device, with an exploded cross sectional view of the site-specific MOSFET device for processing in accordance with the invention, wherein a window is formed at the backside over such site-specific MOSFET device.
Figure 3B:
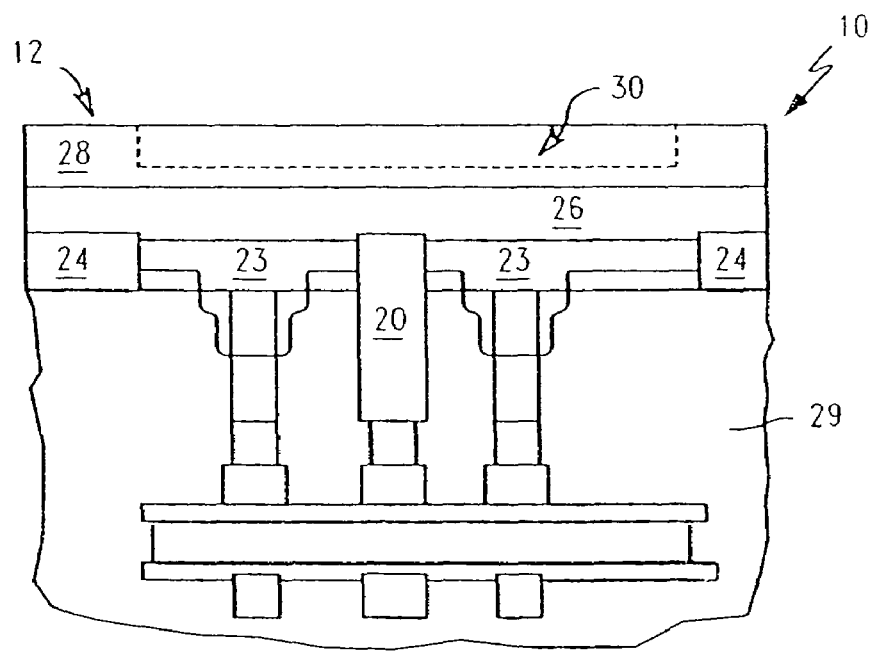
FIG. 3B is a cross sectional view of the exploded site-specific MOSFET device of FIG. 3A showing that "window" or opening of the invention is formed directly over the site specific MOSFET device and over the buried oxide layer.

Referring to FIGS. 3A-B, MOSFET device 10 is shown having a backside 12 thereof for unlayering, i.e., layer removal, to a site-specific MOSFET device as shown within dashed line 16, and its exploded view, of the site-specific MOSFET device. This backside 12 for unlayering may be a backside of a chip, die, wafer fragment, i.e., diced wafer, and the like. As illustrated in a more detail view from the backside of the semiconductor device in FIG. 3B, the site-specific MOSFET device within dashed line 16 may at least include a substrate layer 28, such as silicon, and an insulator layer 26, such as buried oxide layer 26, with a number of front-end-of-line (FEOL) semiconductor features within the insulator layer including, for example, but not limited to, an interconnection plug or via 20, active areas 23 and shallow implant trench insulator junctions 24. The shallow implant junctions 24 are preferably implanted to a depth or thickness of less than about 80 nm, while the gate film is preferably less than about 2 nm in thickness, and may be a material including gate oxide, gate nitride, a high dielectric constant material, and the like.

FIG. 3B further illustrates, from a backside view of the device, the non-planar nature of the front-end-of-line (FEOL) films of the MOSFET device, for which, the present invention is particularly useful in backside unlayering of non-planar FEOL films of the MOSFET device. The non-planar nature of the FEOL films include, for example, the shallow implant trench insulator junctions 24 extending beyond the plane of the active region 23, as well as the interconnection vias 20 extending beyond the plane of the active regions 23. As should be appreciated, other non-planar FEOL features of the MOSFET device may include, but are not limited to, a liner material (not shown) residing between the trench insulator junctions 24 that extends beyond the active regions 23, a circumferential liner (also not shown) surrounding the via 20 extending beyond the active region 23, and the like.

As discussed above, conventional approaches for backside unlayering encounter difficulties in unlayering these non-planar features/films of the device undergoing backside unlayering. Different materials that the FEOL features/films are made of also pose significant challenges for uniform backside unlayering with conventional approaches. Still further, conventional methods of backside unlayering generally involve a high frequency (i.e., 13.56 MHz) RF plasma energy, which can rupture the thin gate dielectric films due to plasma charging effects. The present invention overcomes these problems associated with conventional approaches for backside unlayering by providing a method and apparatus for the uniform backside unlayering of both planar and non-planar features/films, as well as films/features of different materials, of a site specific MOSFET device being processed while maintaining the MOSFET device electrical functionality.

Figure 4A:
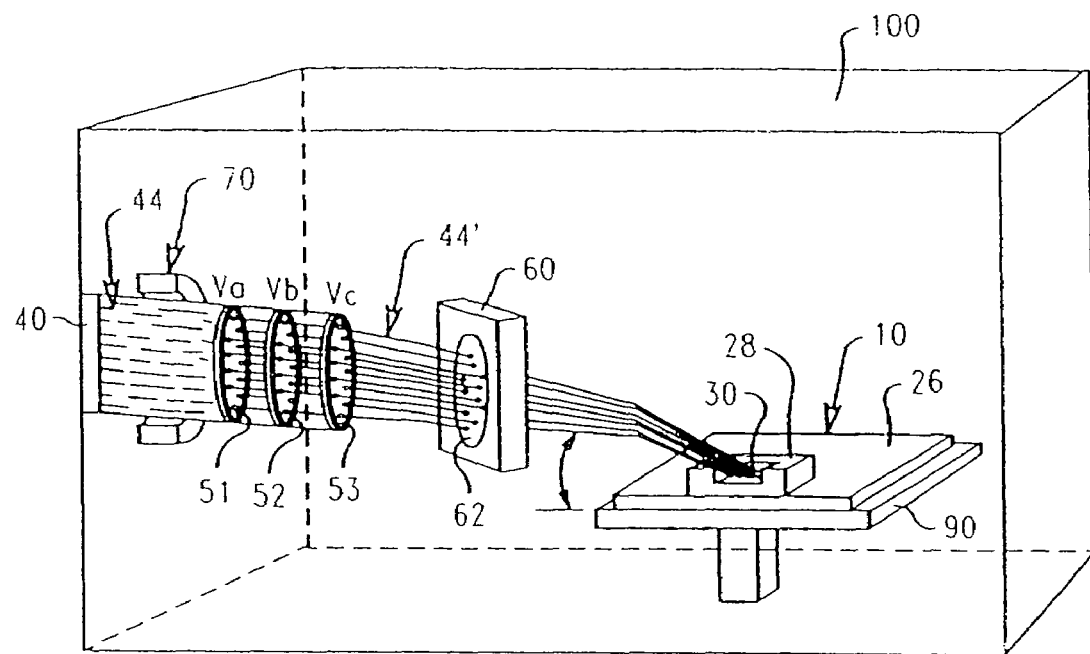
FIG. 4A is an oblique view of the unlayering step of the invention with a low energy inert collimated ion beam being targeted at the MOSFET device backside within the window of FIGS. 3A-B.
Figure 4B:
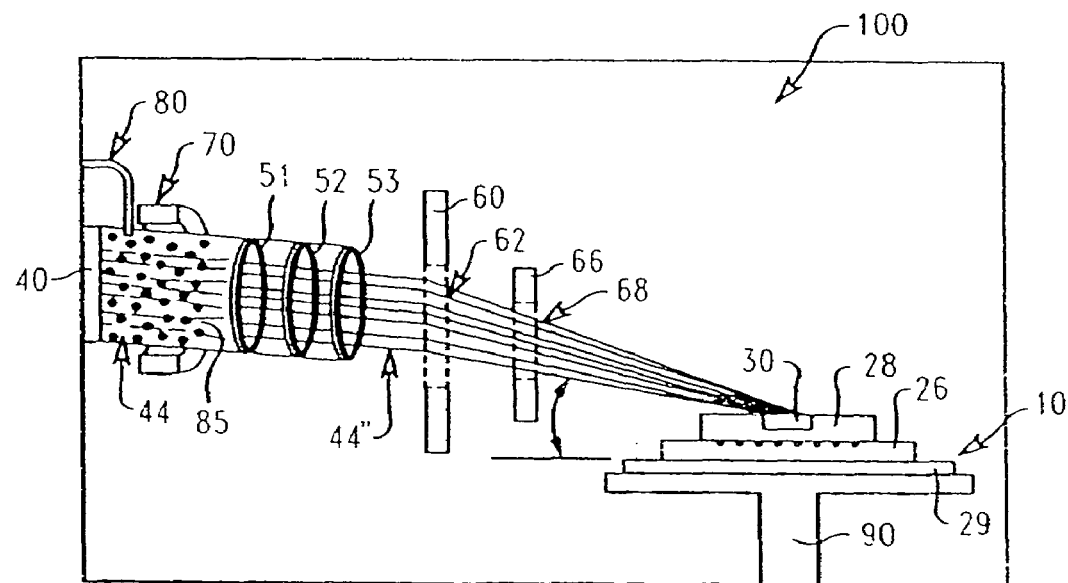
FIG. 4B is a cross sectional view of the unlayering step of the invention with low energy inert collimated ion beams in combination with a gas for Chemical Assisted Ion Beam Etching targeted at the MOSFET device backside within the window of FIGS. 3A-B.

Referring to FIGS. 4A-B, in accordance with the invention, MOSFET device 10 is positioned within a processing chamber 100 for backside processing, such as a ion milling chamber, laser-assisted chemical etching (LCE) chamber, a computer numerically controlled (CNC) milling chamber, and the like. Preferably, processing chamber 100 is an ion milling chamber. Optionally, backside 12 of the MOSFET 10 may be globally thinned. This may be accomplished by globally thinning the backside 12 of the MOSFET 10 prior to entry into the processing chamber 100, or alternatively, globally thinning the backside 12 of the MOSFET 10 within processing chamber 100.

Once within processing chamber 100, an opening or window 30 is formed in the backside of the MOSFET device, preferably in the thinned backside of the MOSFET device 10. Wherein the MOSFET has been thinned, both thinning and the formation of window 30 within the thinned MOSFET may be accomplished within processing chamber 100 by consecutive processing steps. In the preferred embodiment, the MOSFET is thinned via milling within ion milling chamber 100, and then subsequently window 30 is formed in the thinned MOSFET backside within the same milling chamber.

The window is preferably formed in substrate layer 28 of MOSFET device 10, as shown in FIGS. 3A-B, by localized site milling either with laser microchemical etching or computer numerically controlled milling at the backside 12 of MOSFET 10. Window 30 may be milled at the backside of the MOSFET to a depth extending from about 30% to about 80% into the substrate layer 28, preferably from about 30% to about 50% into the substrate layer 28. That is, window 30 does not traverse through substrate layer 28, and as such, it does not contact the underlying buried oxide layer 26 and/or gate film. This window 30 is milled in the substrate layer 28, over the site-specific MOSFET device within dashed line 16 for subsequent electrical and physical characterization thereof. In the preferred embodiment, the window is formed in the thinned substrate layer 28 at the backside of MOSFET 10 to a depth ranging from about 50 µm to about 300 µm, preferably from about 50 µm to about 100 µm, from a top surface of the buried oxide layer 26. Optionally, prior to further processing, any residual silicon may be removed. For example, cesium hydroxide at elevated temperature may be used to selectively remove any single crystal silicon.

An essential feature of the invention is that this further processing occurs only within window 30 at the MOSFET backside such that the invention advantageously allows for maintaining integrity, strength and reliability of the semiconductor device being processed. Additionally, this backside unlayering processing within window 30 avoids any induced stress risks associated with the conventional backside unlayering processes discussed above which remove the entire substrate layer 28 (not just within window 30) to expose the underlying buried oxide layer 26.

In accordance with the invention, once window 30 is formed in the backside of MOSFET 10, the present backside unlayering to expose FEOL features and/or films of MOSFET 10, and in particular unlayering of non-planar FEOL films, proceeds by performing collimated ion beam milling only within window 30 at the backside 12 of the MOSFET.

In so doing, as shown in FIGS. 4A and 4B, MOSFET device 10 resides on a temperature controlled, rotating, tilting stage 90 within processing chamber 100 during the processing in accordance with the invention. The stage 90 may be temperature controlled to temperatures ranging from about −30° C. to about 150° C., preferably from about −5° C. to about 80° C., du uniform backside unlayering processing of the invention. The temperature of stage 90 may be varied in these ranges during the present processing as needed for either accelerating chemical assisted ion milling rates, or alternatively, slowing chemical assisted ion milling rates of the invention.

An ion source 40 also resides within the chamber 100 at a location above a surface area of the MOSFET device to be processed. This ion source may be a source that generates inert ion beams 44 such as, but not limited to, argon, helium, neon, xenon, and the like. At least two, and preferably three collimators 51, 52, 53 also reside within the processing chamber 100. Collimators 51, 52, 53 each include a grid having a plurality of openings such that the openings on collimators 51, 52, 53 are aligned with each other for allowing generated ion beams to pass through each of the collimators for focusing thereof. The collimators may be comprised of molybdenum or a sintered carbon material. Also within processing chamber 100 is a shield 60 having opening 62 positioned in a location or distance above the MOSFET device 10 such that the collimated ion beams 44' pass there-through and are focused to contact the MOSFET device only within window 30.

In the present backside unlayering process, ion source 40 generates low energy inert ion beams, such as those incident beams having energies of about 100 eV (or even lower) to about 650 eV. An R.F. pulsed switch power source is employed to generate these low energy inert ion beams, and as such, any plasma charging issues associated with conventional processing techniques is substantially avoided. For example, conventional high energy ion unlayering processing, such as those having energies of about 6 KeV to 50 KeV, commonly induce plasma charge buildup in the device being processed as a result of inductively coupled plasma sources associated with high energy ion beams, of which the present invention avoids.

Once these inert ion beams 44 are generated, a magnet 70 within chamber 100 resides at a distance substantially close to the ion source for containing the excited plasma, i.e., inert ion beams 44, within a confined area as shown in FIGS.

4A-B. The magnet may have a voltage ranging from about 0.8V to about 2 Volts. The inert ion beams 44 are then drawn toward the collimators having grids aligned to one another. The collimators may be of cathode designs, such as filament or non-filament cathode design, or alternatively, of an RF generated plasma design.

In so doing, collimators 51, 52, 53 have differing voltages Va, Vb, Vc, respectively, ranging from about 0 Volts to 1000 Volts. In particular, the inert ion beams 44 are generated and drawn toward and through collimators 51, 52, 53 sequentially. Wherein the system includes three collimators, ions are drawn toward the first collimator 51, which is at a first voltage (Va). Selected ones of the inert ion beams 44 pass through grid openings of first collimator 51, and are drawn toward the second collimator 52, which is at a higher voltage (Vb) than that of first and third collimators 51, 53 (Va, Vc). The collimated ions then pass through grid openings of the second collimator 52 toward the third collimator 53 at ground (Vc) or zero volts. Thus, wherein three collimators 51, 52, 53 are used, this second collimator is the accelerator grid. However, wherein the system only includes two collimators 51, 52, voltages Va, Vb will be Va being the accelerator and Vb at ground. The net result is a collimated low energy beam ranging from 100 electron volts to 650 electron volts.

The collimated ions 44' pass through aligned grid openings of the last collimator at an accelerated rate, and then through opening 62 in shield 60. This shield 60 having opening 62 is essential to the invention as it focuses the collimated ion beams 44' such that they only contact the MOSFET within window 30 for further backside unlayering in accordance with the invention.

Alternatively, as shown in FIG. 4B, prior to passing through collimators 51, 52, 53, the low energy inert ion beams 44 may be mixed with gas 85 from gas source 80, such as a gas nozzle or delivery needle. This gas source preferably extends into the path of the ion beams 44 for providing the computer controlled mass flow controlled gas stream for Chemical Assisted Ion Beam Etching (CAIBE). The resultant combination 44" of collimated ion beams 44' and gas 85 advantageously enables backside unlayering processing of different semiconductor materials, in addition to the non-planarity of such differing materials, of the MOSFET within window 30. The gas flow is preferably a chlorinated or fluorinated gas, such as, CF4, SF6, CHF3, or CF4 gases, introduced into the processing chamber at a flow rate of less than about 200 SCCM to chemically assist the ion milling removal of dissimilar materials from backside 12 of the device. That is, these gas chemistries interact with the inert ion beam to selectively remove layers of buried oxide material on a rotating, tilting sample as discussed further below.

Thus, in the invention, both collimated ion beams 44' and combination 44" collimated ion beams and gas are generated using the cathode source or RF energy source comprising collimators 51, 52, 53 having parallel, aligned conductive grids, preferably, measuring over about 8 cm in diameter. The resultant collimated ions 44', 44" have low energies (e.g., ranging from about 100 eV to about 650 eV) and beam diameters greater than about 8 cm with variable Gaussian distribution high current densities, such as 300 uA/cm$^2$.

The collimated ion beams 44' as shown in FIG. 4A, or alternatively the mixture of collimated ion beams 44" with gas 85 as shown in FIG. 4B, then pass through an opening 62 of shield 60 to focus the collimated ion beams, with or without gas 85, only within window 30. That is, the low energy inert collimated ion beams, such as those ranging from about 100 eV (or even lower) to about 650 eV, are locally targeted at the MOSFET device backside through shielding opening 62 so as to contact only the substrate layer 28 within window 30 for unlayering substrate layers therein, including any non-planar features. In so doing, the shield 60 protects exposed surface areas of the MOSFET that are adjacent to the window 30 from exposure to and contact with the present low energy inert incident beams.

In addition to shielding 60 focusing the low energy inert collimated ion beams and gas to only within window 30, the temperature controlled rotating, tilting stage 90, to which MOSFET 10 is affixed, further enhances complete planar ion beam/CAIBE combination removal of substrate layering within window 30. This tilting, rotating stage 90 allows for complete rotation and sufficient tilting of the MOSFET so that the ion beam and gas can directly and entirely contact all exposed surface areas only within window 30, including any non-planar features, for the unlayering thereof. The temperature controlled rotating tilting stage significantly decreases any localized heating of device being processed, such that it further avoids any undesirable affects on the device properties associated with localized heating of the device, such as those affects including undesirable changes to the strained silicon junction characteristics, polysilicon gate materials, or to interconnections.

The collimated ion beams, with or without gas 85, contact surfaces of MOSFET within window 30 at an incident angle ranging from about 0 degrees to about 90 degrees, preferably at angles ranging from 8 degrees to about 24 degrees. As the stage rotates and tilts, the incident angle at which the collimated ion beams, with or without gas 85, contact the MOSFET may vary during processing in accordance with the invention.

The angle of incident of collimated ion beams 44', 44" is dependent upon the depth of the window to be formed in the backside of the thinned device 10. In this aspect of the invention, the larger the incident angle of the ion beam, with respect to the MOSFET surface in window 30 being processed, the deeper window 30 is formed into substrate layer 28. Likewise, the smaller the incident angle, the shallower window 30 is formed in substrate layer 28. Additionally, the present backside unlayering process may be further enhanced by including use of a fiber optic ruby crystal computer controlled photo spectrometer for optical endpoint detection to control the unlayering within window 30.

Optionally, removal of material within window 30 may be enhanced by further including a second shield 66 with second opening 68 in chamber 100 to defocus the larger collimated ion beam emitted through opening 62 of shield 60 to a smaller diameter collimated ion beam for contacting MOSFET. For example, shield 66 may have opening 68 with grid diameters of about 1 mm to about 100 mm in diameter to defocus the larger 8 cm collimated ion beam emitted through opening 62 prior to contacting MOSFET 10 within window 30.

Figure 2:
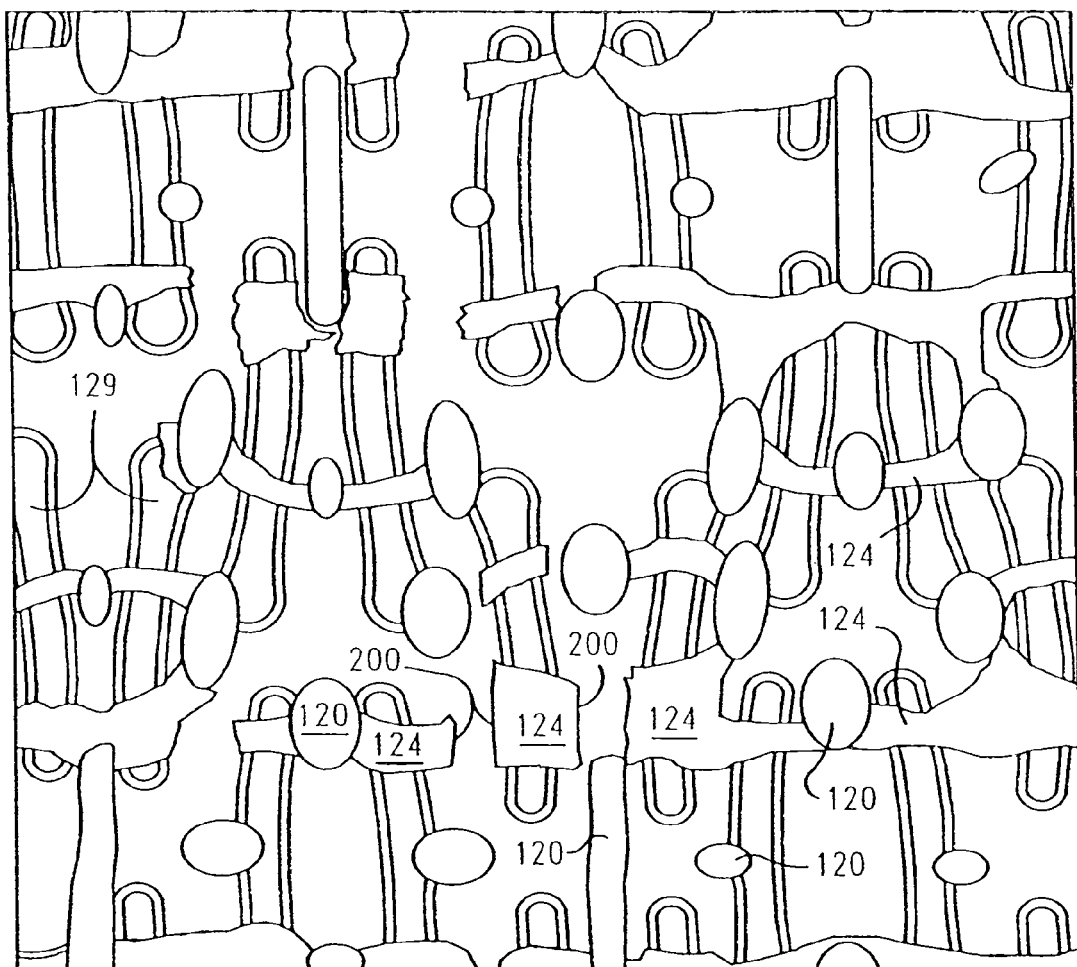
FIG. 2 is a prior art backside view of the unlayered SOI MOSFET of FIG. 1 showing entire regions of the implant regions of the various MOSFET devices undercut and damaged, rendering the MOSFET devices under investigation non-functional for any subsequent electrical characterization.
Figure 5:
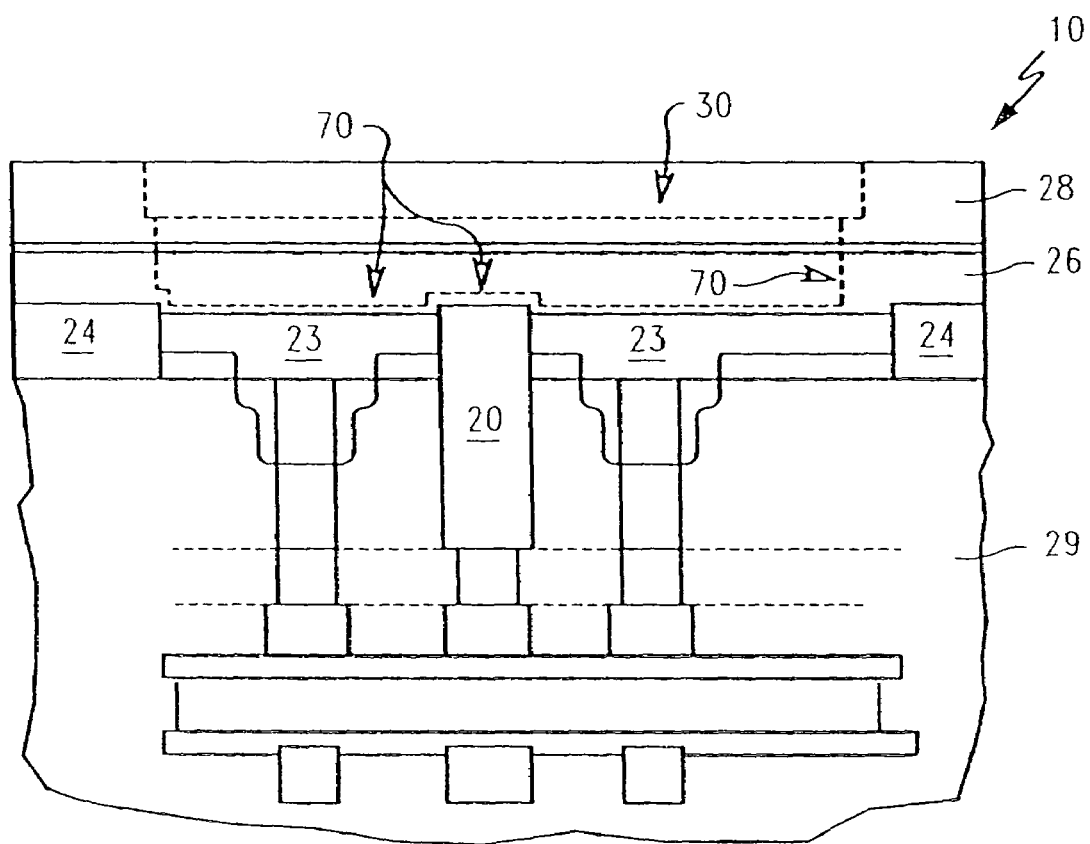
FIG. 5 is a backside cross sectional view showing the MOSFET device of FIGS. 4A-B upon completion of the backside unlayering of the non planar features in accordance with the invention, such that the device has been unlayered down to its active area without damaging device structures, such as the thin gate films, as well as backside unlayering of the MOSFET device to expose the FEOL via for subsequent electrical characterization.
Figure 6:
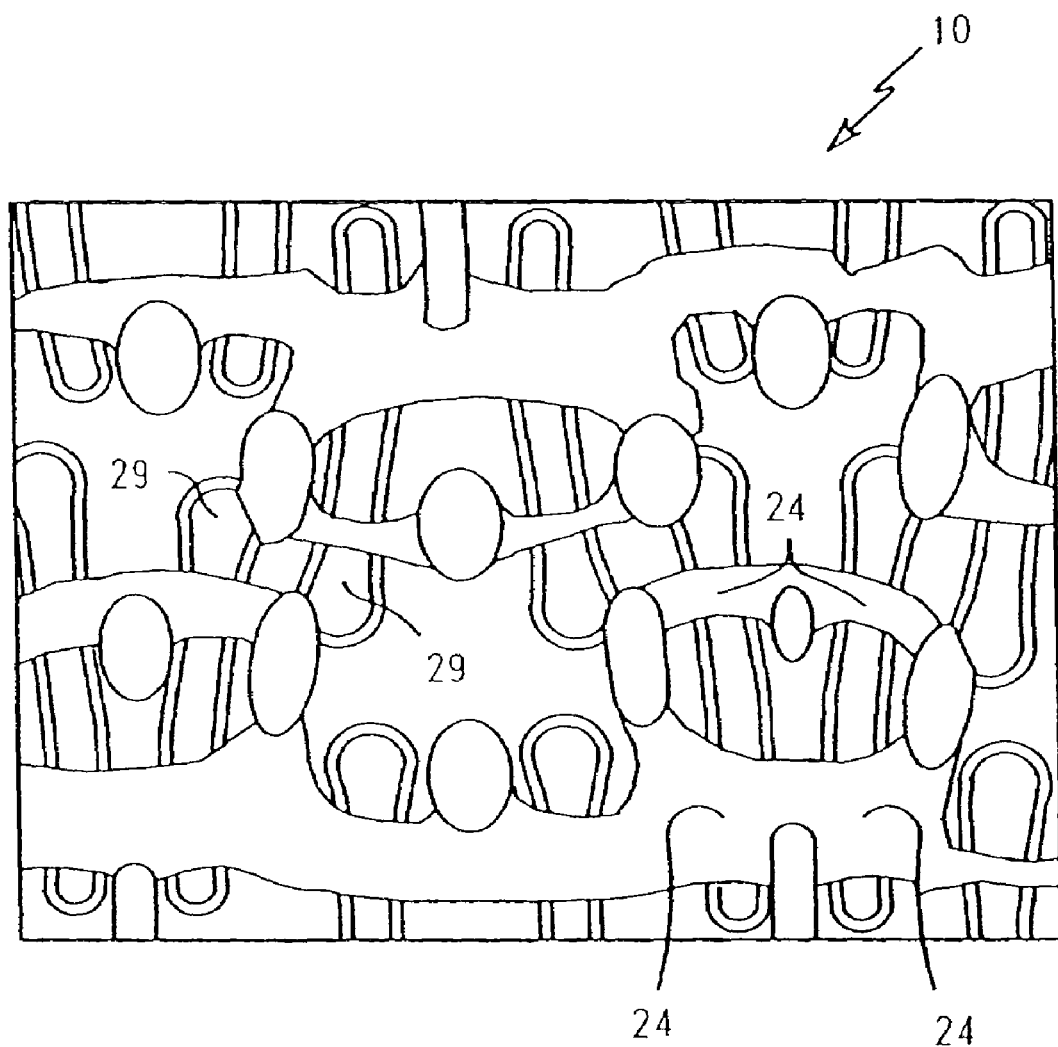
FIG. 6 is a backside unlayered schematic drawing showing the results of the present conformal backside unlayering of non-planar surfaces of the MOSFET device of FIG. 5, depicting the absence of any undercutting of active silicon (implant regions) areas while maintaining device functionality in accordance with the invention.

As shown in FIGS. 5 and 6, the device 10 has been unlayered to provide a conformal collimated ion milled surface 70 of MOSFET 10 down to its active area 23 without damaging device structures, such as the thin gate films, as compared to the damaged areas of the prior art illustration of FIG. 2. The desired anistropic or isotropic substrate material is removed such that residual ionic species on the device are avoided in comparison that of FIG. 2. Once exposed, the FEOL vias may further undergo subsequent backside processing, including AFM contact probing, AFP probing, AFM non-contact capacitive probing, sub-micron tungsten filament probing, to permit linear threshold voltage measurements, saturated voltage measurements of the MOSFET features exposed from the backside of device to facilitate subsequent electrical characterization.

Thus, in accordance with the invention, the present low energy inert ion milling selectively removes layers of buried oxide material of device 10, which is being simultaneously cooled by the temperature controlled stage 40, and rotated and tilted on stage 40, to ultimately achieve backside unlayering planarity of MOSFET device 10. This backside unlayering planarity may be achieved with or without chemical assisted ion beam etching using gas chemistries that interact with the low energy inert ions. The present invention backside unlayering via low energy ion beams having high current densities avoids any undesirable damaging affects to the strained silicon junctions, thin gate oxide and high-k dielectric gate films associated with conventional unlayering approaches that heat device 10, as well as avoids any metallic ion implantation, surface amorphization damage and gallium surface contamination problems association with conventional metallic ion source high accelerated beam systems.

The invention advantageously avoids any antistrophic characteristics associated with conventional unlayering processes by providing for low energy inert ion beam milling, optionally in combination with CAIBE etching, for the selective removal of substrate layers to expose FEOL features and/or films for further processing. The present CAIBE/collimated low energy inert ion milling successfully removes substrate layering down to the active silicon implant junction levels without damaging the thin gate films, i.e., those less than 2 nm in thickness. It also exposes the FEOL features, such as tungsten vias, that extend beyond the active silicon implant junction regions. In so doing, a critical feature of the invention is that the incident ion beam processing of the invention does not affect strained silicon junction regions of the device active areas, as compared to those conventional processing techniques, such as heat generated by incident gallium ion beams or the uncontrolled isotropic etch attack effects of wet etch chemistries, such as Br2, XeF2, Cl2 gas, which damage strained silicon junction regions as is shown in the prior art illustrations of FIGS. 1 and 2.

Further, the present methods and apparatus as applied to backside unlayering of MOSFET devices successfully overcome the problems of maintaining full die functionality associated with conventional backside unlayering techniques, as well as satisfies the need for site specific MOSFET device access via backside thinning for modern technology. The invention overcomes problems associated with conventional backside thinning approaches associated with FIB microscopy including, but not limited to, problems associated with the high accelerating voltage charged particle beams, high charge buildup and/or damage to MOSFET thin gate dielectric films from high acceleration beams, RF plasma/reactive ion etch induced charging or rupturing of thin gate dielectric films, as well as avoiding affects of implantation of highly energetic ions, such as gallium, indium and aluminum ions, into the substrate or junction FEOL structures.

That is, the present invention eliminates any affects induced by surface amorphization damage associated with high accelerating beam potential (>1 KeV to 300 KeV) of conventional FIB microscopy processing, as well as avoids any charge-induced damage associated with RF plasma sources or those associated with FIB systems, such as those using gallium, indium or aluminum ions. It avoids any contamination of exposed surface areas, undercutting, charge buildup, ion implantation and/or amorphization damage to the MOSFET device surface structures, all of which are commonly associated with conventional unlayering processes, such as the results thereof shown in FIGS. 1 and 2, that employ the use of positively charged focused ion beams of high acceleration voltages, such as those having energies of about 30 KeV and even higher.

Further, a critical feature of the invention is that it addresses and efficiently delayers, from a backside of the device, any non-planar features encountered in the MOSFET device being subjected to unlayering in accordance with the invention. The invention even delayers dissimilar, non planar features or films located on the MOSFET such as any combination of non planar film materials including, but not limited to, tungsten, titanium nitride, silicon nitride, heavily doped silicon, buried oxide films, shallow trench insulator films, high density plasma deposited oxide, high density plasma deposited nitride, chemical vapor deposited tetraorthosilicate films and combinations thereof. That is, the methods and apparatus of the invention account for the dissimilar materials and non planarity of FEOL films in order to permit direct access sub micron contact probing, contact AFM probing, AFP probing, SPM probing of FEOL MOSFET devices for electrical characterization from backside of the die/wafer.

An essential feature of the invention is that further processing occurs within window 30 in substrate layer at the backside of the MOSFET device such that the invention advantageously allows for maintaining integrity, strength and reliability of the semiconductor device being processed. Additionally, this backside unlayering processing only within the window 30 avoids any induced stress risks associated with conventional backside unlayering processes as discussed above which remove the entire substrate layer 28 (not just within window 30) to expose the underlying buried oxide layer 26.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of processing a backside of a semiconductor device comprising:
   providing a semiconductor within a processing chamber, said semiconductor having a substrate layer at a backside surface of said semiconductor;
   forming a window into said substrate layer at said backside surface of said semiconductor such that said window resides within said substrate layer;
   generating a collimated ion plasma within said processing chamber;
   focusing said collimated ion plasma so as to contact said semiconductor only within said window by passing said collimated ion plasma through an opening in a shield within said processing chamber;
   contacting said semiconductor in said window with said focused collimated ion plasma to uniformly remove a portion of said semiconductor for exposing semiconductor features in a location on said semiconductor corresponding to said backside window.

2. The method of claim 1 wherein said processing chamber is selected from the group consisting of an ion milling chamber, laser-assisted chemical etching chamber, and a computer numerically controlled milling chamber.

3. The method of claim 1 further including the step of thinning said backside of said semiconductor prior to forming said window.

4. The method of claim 1 wherein said semiconductor features comprise a plurality of features of differing materials.

5. The method of claim 4 wherein said differing materials are selected from the group consisting of tungsten, titanium nitride, silicon nitride, doped silicon, buried oxide films, shallow trench insulator films, high density plasma deposited oxide, high density plasma deposited nitride, CVD tetraorthosilicate films and combinations thereof.

6. The method of claim 1 wherein said collimated ion plasma has an energy ranging from about 100 eV to about 650 eV.

7. The method of claim 1 wherein said step of generating said collimated ion plasma within said processing chamber comprises:
   providing an ion source within said processing chamber;
   providing a first collimator and a second collimator within said processing chamber;
   generating an ion plasma from said ion source;
   passing said ion plasma through said first and second collimators to generate said collimated ion plasma.

8. The method of claim 7 wherein said ion source is selected from the group consisting of argon, helium, neon and xenon.

9. The method of claim 7 further including providing a third collimator within said processing chamber for generating said collimated ion plasma.

10. The method of claim 7 further including a magnet for controlling said ion plasma prior to passing through said first and second collimators.

11. The method of claim 1 further including a gas mixed with said collimated ion plasma for chemical assisted ion etching said semiconductor only within said window.

12. The method of claim 1 wherein said collimated ion plasma contacts said semiconductor only within said window at an incident angle ranging from about 0 degrees to about 90 degrees.

13. The method of claim 1 wherein said window is milled into said substrate layer to a depth extending from about 30% to about 80% into said substrate layer.

14. The method of claim 13 wherein said substrate layer is thinned prior to forming said window, such that, said window is milled into said thinned substrate layer.

* * * * *